United States Patent [19]

Shen et al.

[11] Patent Number: 5,347,063
[45] Date of Patent: Sep. 13, 1994

[54] METHOD FOR DIRECT ARYLATION OF DIAMONDOIDS

[75] Inventors: Dong-Min Shen, Langhorne, Pa.; Orville L. Chapman, Los Angeles, Calif.; Ling Lin, Los Angeles, Calif.; Rafael Ortiz, Los Angeles, Calif.

[73] Assignee: Mobil Oil Corporation, Fairfax, Va.

[21] Appl. No.: 28,458

[22] Filed: Mar. 9, 1993

[51] Int. Cl.5 .............................. C07C 13/28
[52] U.S. Cl. .................... 585/352; 585/375
[58] Field of Search .................. 585/352, 375

[56] References Cited

U.S. PATENT DOCUMENTS

| | | | |
|---|---|---|---|
| 3,457,318 | 7/1969 | Capaldi et al. | 260/666 |
| 3,560,578 | 2/1971 | Schneider | 260/648 |
| 3,563,919 | 2/1971 | Schneider | 585/352 |
| 5,019,660 | 5/1991 | Chapman et al. | 585/22 |
| 5,053,434 | 10/1991 | Chapman | 521/52 |

OTHER PUBLICATIONS

Chem. Listy, 51, 2335, 1957 (Chem. Abstract 52:6213a).
Collect. Czech. Chem. Commun. 24, 1959 (Chem. Abstract 53:7045b).
Synthesis, 692, 1972.
J. Labelled Compd. Radiopharm 1991, 29(7), 841–6 (Chem. Abst. 115:114119u).

*Primary Examiner*—Asok Pal
*Attorney, Agent, or Firm*—Alexander J. McKillop; Dennis P. Santini; Robert B. Furr, Jr.

[57] ABSTRACT

The present invention provides a method for arylating a non-halogenated diamondoid compound comprising the steps of:

(a) providing a non-halogenated diamondoid compound or mixture of non-halogenated diamondoid compounds and an aromatic compound or mixture of aromatic compounds wherein at least one diamondoid compound and at least one aromatic compound are at least partially miscible;

(b) mixing the compounds of step (a) to form at least a partial solution;

(c) adding a reactive halide source to the mixture of step (b);

(d) adding a Lewis acid to said mixture of step (c);

(e) heating said mixture of step (d) to temperature above ambient and holding said heated mixture at elevated temperature;

(f) recovering an arylated diamondoid compound from said solution.

17 Claims, 10 Drawing Sheets

METHOD FOR DIRECT ARYLATION OF DIAMONDOIDS

FIELD OF THE INVENTION

This invention relates to the functionalization of polycyclic alkanes. More particularly, this invention provides a method for the direct arylation of diamondoids.

BACKGROUND OF THE INVENTION

Diamondoid compounds can be converted to their aryl-substituted derivatives in two steps by first halogenating the diamondoid compound and then replacing the halogen with an aryl group. The two-step conversion, requiring separation of an intermediate halogenated organic product, is effective on a bench scale, but the necessary intermediate product separation step has proven to be an obstacle to commercialization of the process on an industrial scale. Thus it would be desirable to provide a method for converting non-halogenated diamondoid compounds to their arylated derivatives which could readily operate in a single vessel in the absence of halogenated diamondoid feedstock.

The term "diamondoid" is used in its usual sense, to designate a family of polycyclic alkanes including adamantane, diamantane, and triamantane, as well as the higher analogs and their substituted derivatives, examples of which include ethyl- and methyl-substituted diamondoids. For a survey of the chemistry of diamondoid molecules, see Fort, Raymond C., *Adamantane, The Chemistry of Diamond Molecules* (1976) as well as U.S. Pat. Nos. 5,019,660 to Chapman and Whitehurst and 5,053,434 to Chapman. Arylated diamondoids are useful as heat transfer fluids, lubricants, traction fluids, and chemical intermediates. Adamantane has been found to be a useful building block in the synthesis of a broad range of organic compounds, as exemplified by the following references.

U.S. Pat. No. 3,457,318 to Capaldi et al. teaches the preparations of polymers of alkenyl adamantanes useful as coatings, electrical appliance housings, and transformer insulation. The process, yielding polymers bonded through the tetrahedral bridgehead carbons, comprises contacting an adamantyl halide in the presence of a suitable catalyst with a material selected from the group consisting of substituted allyl halides and olefins to produce adamantyl dihaloalkanes or adamantyl haloalkanes as an intermediate product. The intermediate product is then dehalogenated or dehydrohalogenated, respectively, to produce the alkenyl adamantane final product.

U.S. Pat. No. 3,560,578 to Schneider teaches the reaction of adamantane or alkyladamantanes with a $C_3$-$C_4$ alkyl chloride or bromide using $AlCl_3$ or $AlBr_3$ as the catalyst. The reference describes polymerization through $C_3$-$C_4$ linkages connecting bridgehead carbon atoms in the starting adamantane hydrocarbon; See column 3, lines 35-55, as well as the structural illustrations in columns 3-5. Coupling adamantane nuclei through $C_3$-$C_4$ linkages is quite different than arylating diamondoid compounds, and the illustration bridging columns 3 and 4 of the Schneider patent clearly shows the production of a halogenated product. The Schneider patent further teaches that primary or secondary alkyl halides are distinctly preferred. Column 5 at lines 12-16.

Landa et al. reported preparation of 1-phenyl adamantane in relatively low yield by heating 1-bromoadamantane with benzene and sodium. Chem. Listy, 51, 2335, 1957 (Chem. Abstract 52:6213a); Collect. Czech. Chem. Commun. 24, 93, 1959 (Chem. Abstract 53:7045b).

Settler et al. improved the yield of the 1-bromoadamantane/benzene reaction by using ferric chloride as the catalyst. Chem. Ber. 92, 1629, 1959.

Newman used 1-bromoadamantane, benzene, t-butyl bromide, and aluminum chloride to prepare 1-phenyl adamantane, 1,3-diphenyl adamantane, 1,3,5-triphenyl adamantane, and 1,3,5,7-tetraphenyl adamantane. Synthesis, 692, 1972.

More recently, Pilgram et al. disclosed the use of 1-acetoxyadamantane in the arylation of diamondoids. Eur. Pat. Appl. EP 358,574 (Chem. Abstract 113:58678v); J. Labelled Compd. Radiopharm 1991, 29(7), 841-6 (Chem. Abstract 115:114119u).

SUMMARY OF THE INVENTION

The present invention provides a method for arylating a diamondoid compound comprising the steps of:

(a) providing a non-halogenated diamondoid compound or mixture of non-halogenated diamondoid compounds and an aromatic compound or mixture of aromatic compounds wherein at least one diamondoid compound and at least one aromatic compound are at least partially miscible;

(b) mixing the compounds of step (a) to form at least a partial solution;

(c) adding a reactive halide source to the mixture of step (b);

(d) adding a Lewis acid to said mixture of step (c);

(e) heating said mixture of step (d) to temperature above ambient and holding said heated mixture at elevated temperature;

(e) recovering an arylated diamondoid compound from said solution.

The aromatic compound is preferably provided in the form of an aromatic solvent which is present in molar excess with respect to the diamondoid compound or mixture of diamondoid compounds. Alkyl halides are preferred reactive halide sources, although any reactive halide such as tertiary, benzyl, or an allylic halide is also effective. Tertiary alkyl halides are particularly preferred.

Examples of useful Lewis acids include $FeCl_3$, $SnCl_4$, $ZnCl_2$, $TiCl_4$, $FeBr_3$, $SnBr_4$, $ZnBr_2$, and $TiBr_4$. $AlCl_3$ is a particularly preferred Lewis acid.

Reaction temperatures of from about ambient to about 250° C. are useful, and temperatures of from about 75° to about 125° C. are preferred. To selectively synthesize 4,9-diphenyl-diamantane, t-butyl halide is the preferred reactive halide source, $AlCl_3$ or $AlBr_3$ is the preferred Lewis acid, and the reactants are present in molar ratios of t-butyl halide to non-halogenated diamantane of from about 1.5:1 to about 4:1. To selectively synthesize 1,4,6,9-tetraphenyl-diamantane, similar conditions may be used with a higher molar ratio of t-butyl halide to non-halogenated diamantane, typically within the range of from about 2:1 to about 5:1.

EMBODIMENTS

The method of the invention is useful for arylating both substituted and unsubstituted diamondoid compounds by the addition of at least one aromatic group to at least one bridgehead position of a diamondoid compound. The aryl group may comprise any suitable aromatic, examples of which include radicals derived from the following aromatic compounds: benzene, toluene, xylenes, ethyl benzene, n-propyl benzene, cumene, n-butyl, i-butyl, and sec-butyl benzenes; thiophene, furan, naphthalene, and similar aromatic compounds.

EXAMPLES

Examples 1–5 were conducted in accordance with the following general procedure.

The diamondoid hydrocarbon was dissolved in an excess amount of an aromatic solvent as arylating reagent in a four-necked flask fitted with a reflux condenser having an $N_2$ bubbler, a pressure-equalized addition funnel containing t-butyl bromide, a mechanical stirrer, and a thermometer. The mixture was stirred and heated in an oil bath at about 80°–90° C. A small portion of the t-butyl bromide was added to the flask followed by anhydrous $AlCl_3$ catalyst added from the top of the condenser. A vigorous reaction ensued, indicated by the release of a large amount of gases from the bubbler (HBr and isobutane). If the reaction did not start, small portions of t-butyl bromide and $AlCl_3$ catalysts were added until it did. Before the initial reaction subsided, the remainder of the t-butyl bromide in the funnel was added at such a rate to sustain the reaction but do not cause it to proceed too vigorously. After all the bromide was added, the mixture was heated and stirred for an additional period of 20 to 120 minutes to ensure the completion of the reaction. After cooling down the mixture, it was transferred into a separatory funnel and washed in turn with dilute aqueous HCl, water, and saturated brine. Removal of solvents by rotary evaporation after drying with anhydrous $Na_2SO_4$ gave the arylated diamondoids. The product was further purified by vacuum fractionation and/or Kugelrohr short-path distillation.

EXAMPLE 1

Figure 1:
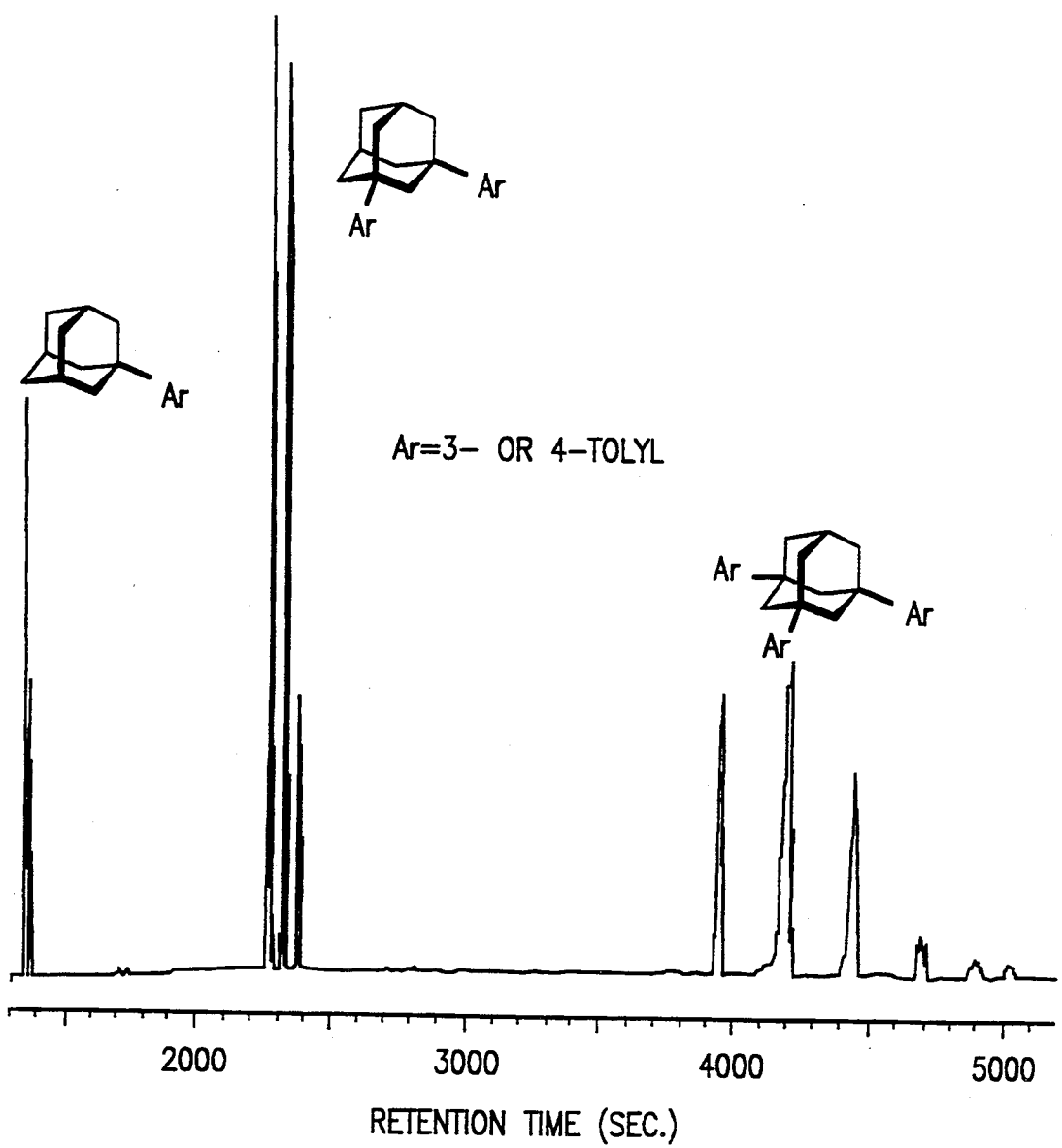
FIG. 1 is a gas chromatogram of the product mixture of Example 1.

Using the above general procedure, the reaction of 1.36 g of adamantane with 3.69 g of t-butyl bromide in 70 mL of toluene with 0.12 g of $AlCl_3$ gave 3.55 grams of oil after purification, with an average degree of arylation of 2.3 based on GC analysis. The gas chromatogram of the product oil is shown in FIG. 1.

EXAMPLE 2

Figure 2:
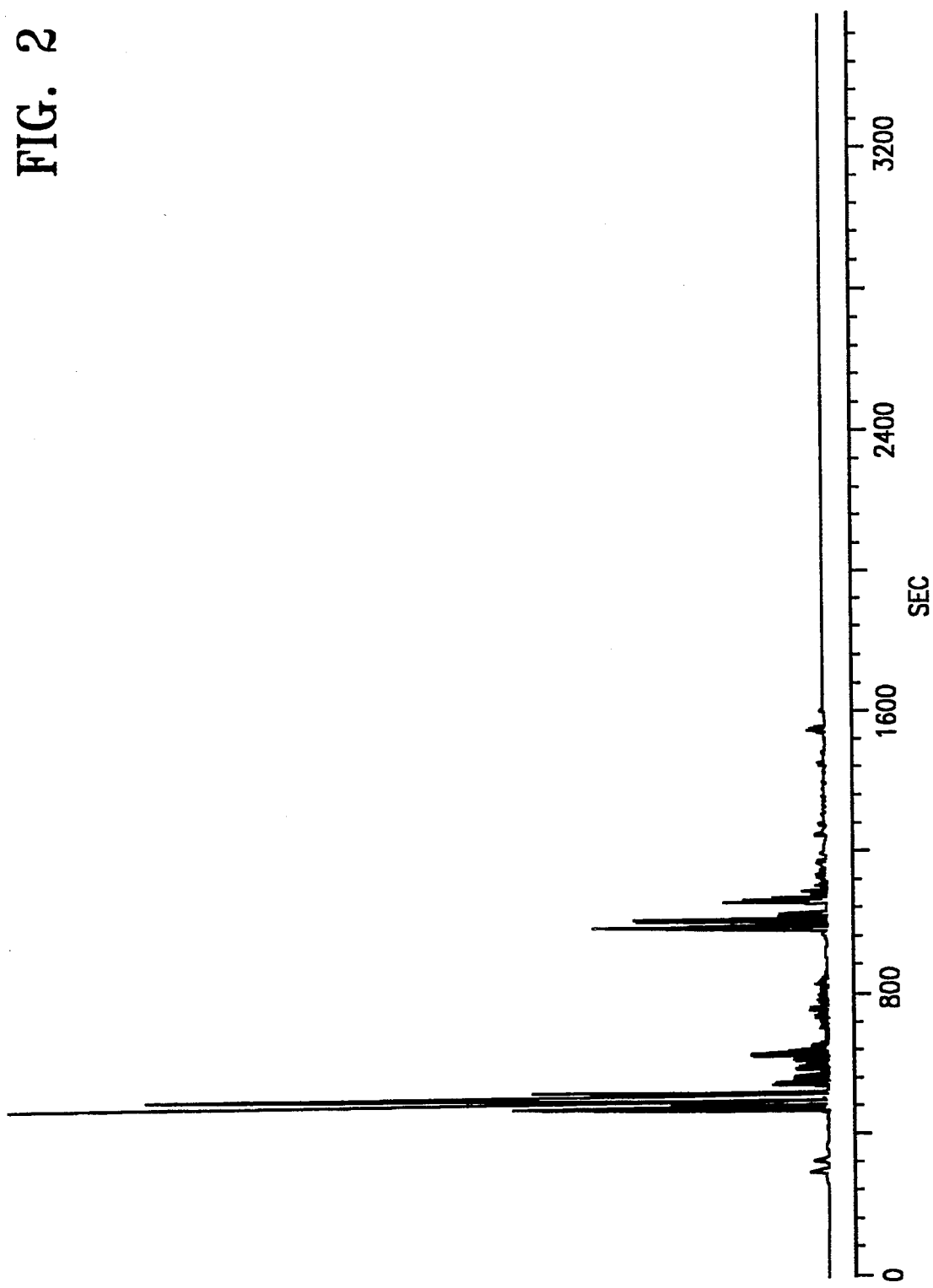
FIG. 2 is a gas chromatogram of the the diamondoid reactant mixture of Examples 2-5.
Figure 3:
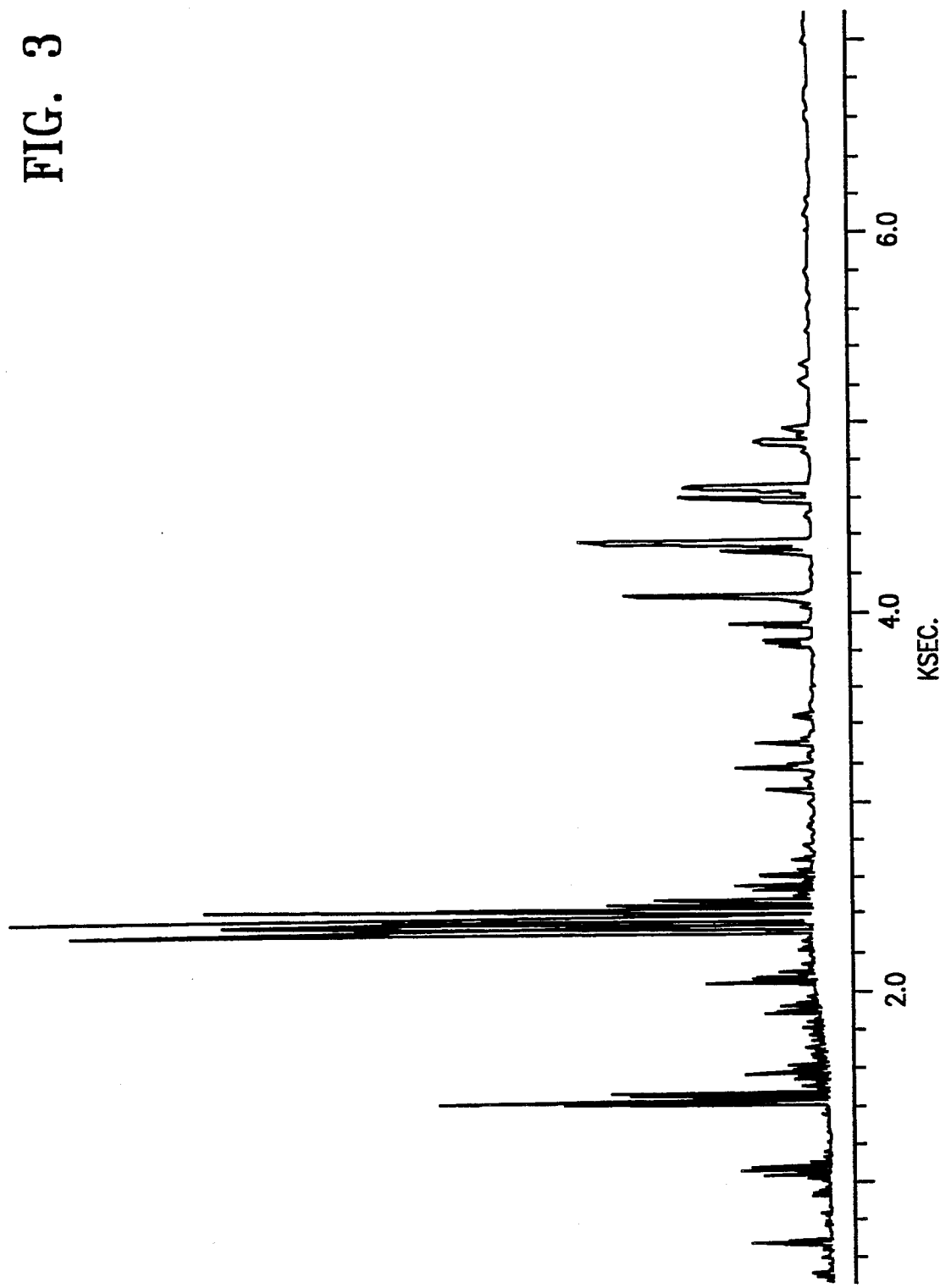
FIG. 3 is a gas chromatogram of the arylated diamondoid product mixture (oil) of Example 2.
Figure 4A:
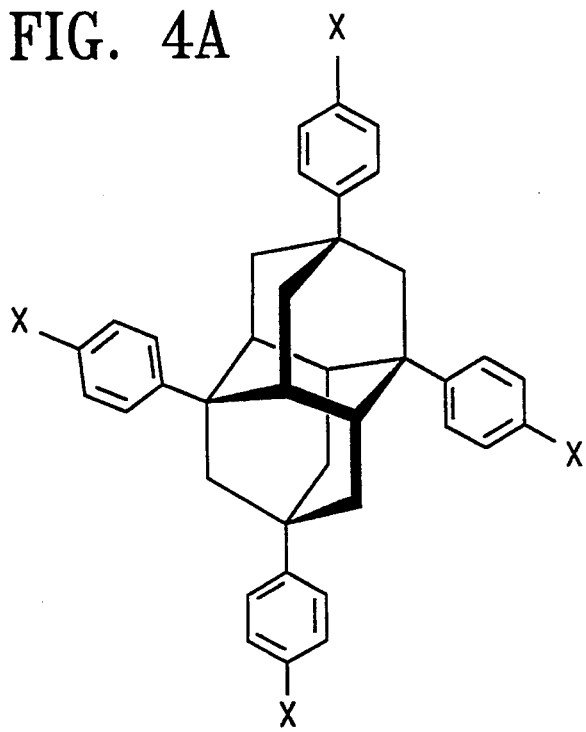
FIG. 4A is a simplified structural diagram of a 1,4,6,9-tetraphenyldiamantane containing a substitutent X on the phenyl group as defined herein.
Figure 4B:
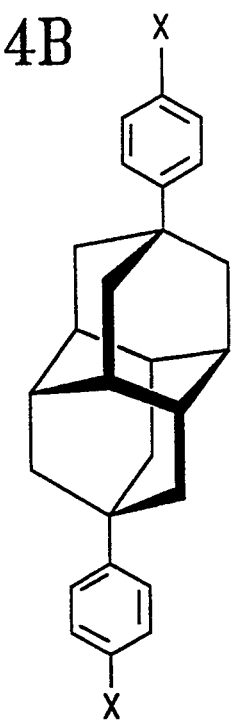
FIG. 4B is a simplified structural diagram of a 4,9-diphenyldiamantane containing a substitutent X on the phenyl group as defined herein.
Figure 4C:
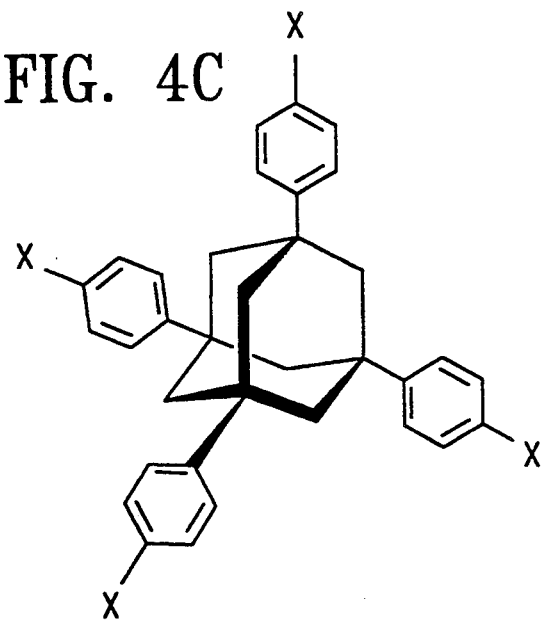
FIG. 4C is a simplified structural diagram of a 1,3,5,7-tetraphenyladamantane containing a substitutent X on the phenyl group as defined herein.
Figure 5:
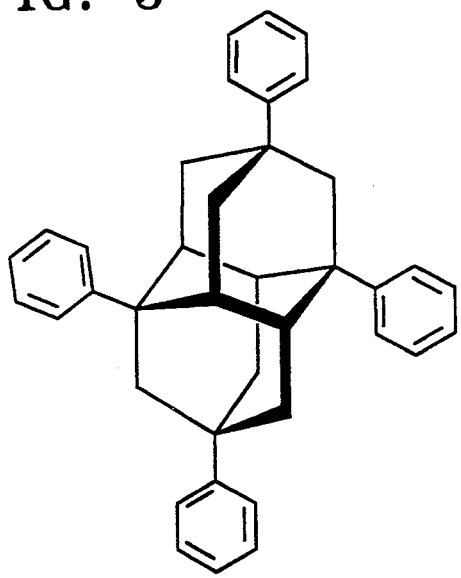
FIG. 5 is a simplified structural diagram of 1,4,6,9-tetraphenyldiamantane as synthesized in Example 6.
Figure 6:
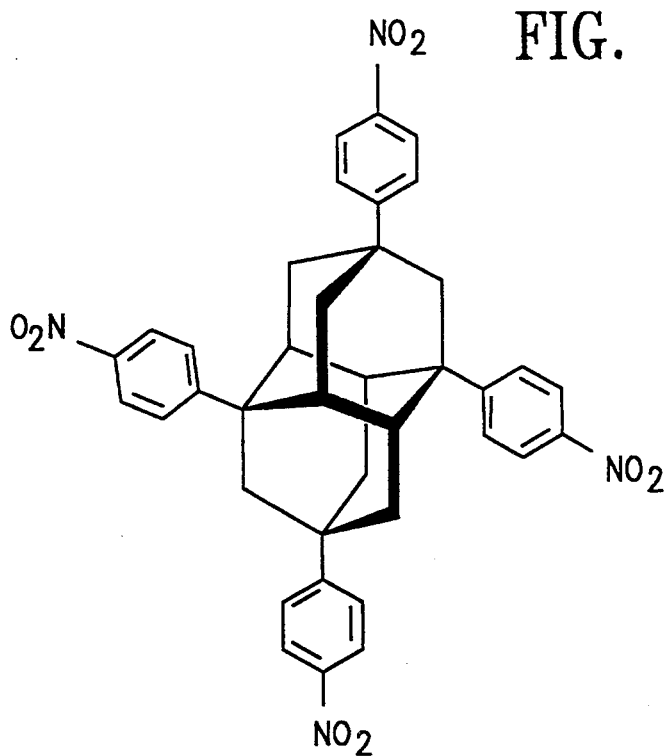
FIG. 6 is a simplified structural diagram of 1,4,6,9-tetra(4-nitrophenyl)diamantane as synthesized in Example 7.
Figure 7:
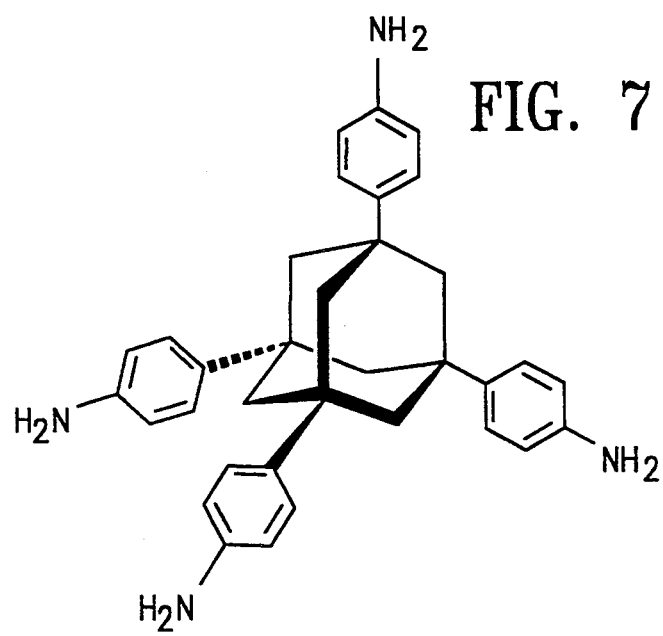
FIG. 7 is a simplified structural diagram of 1,4,6,9-tetra(4-aminophenyl)diamantane as synthesized in Example 8.
Figure 9:
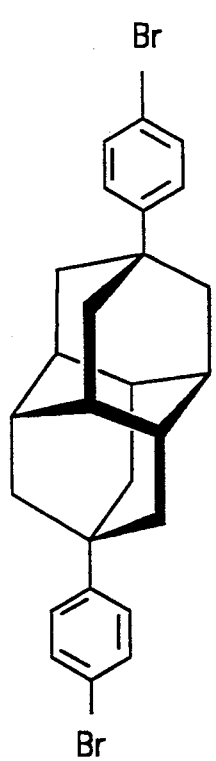
FIG. 9 is a simplified structural diagram of 4,9-di(4-bromophenyl)diamantane as synthesized in Example 10.
Figure 8:
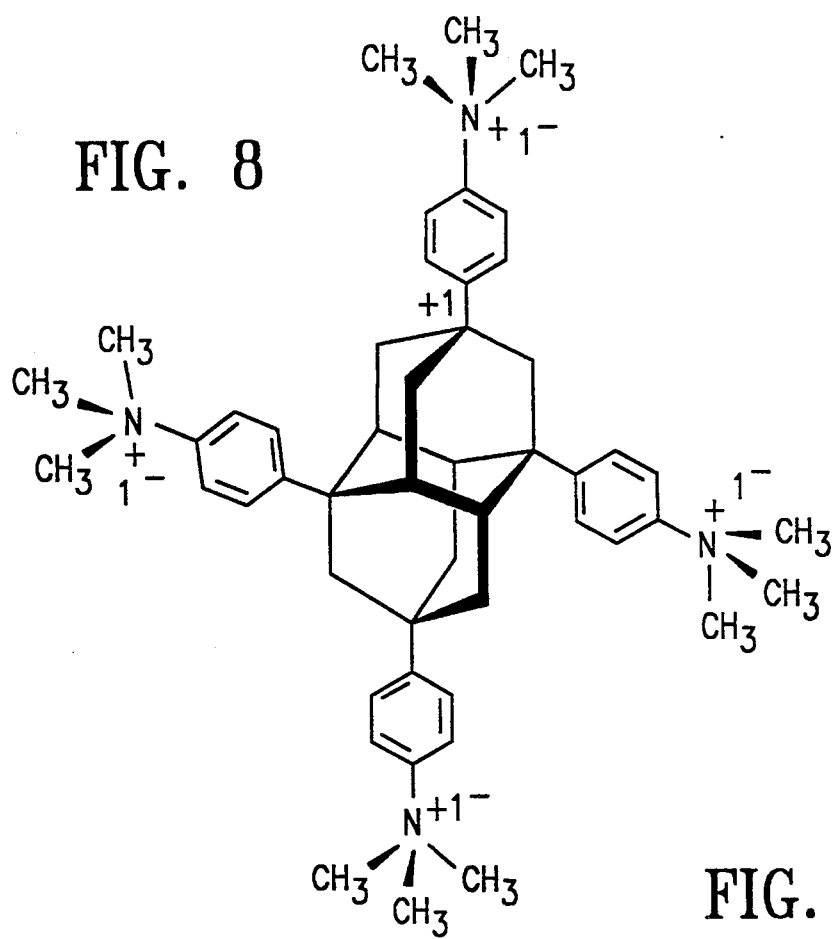
FIG. 8 is a simplified structural diagram of 1,4,6,9-tetra(4-phenyltrimethylammoniumiodide)diamantane as synthesized in Example 9.
Figure 10:
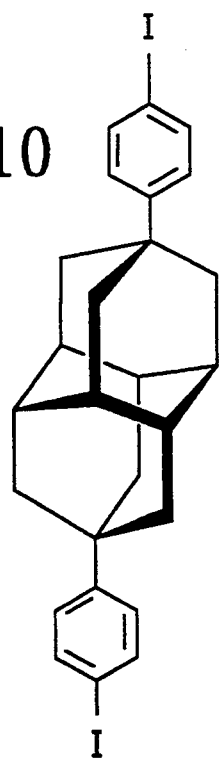
FIG. 10 is a simplified structural diagram of 4,9-di(4-iodophenyl)diamantane as synthesized in Example 11.
Figure 11:
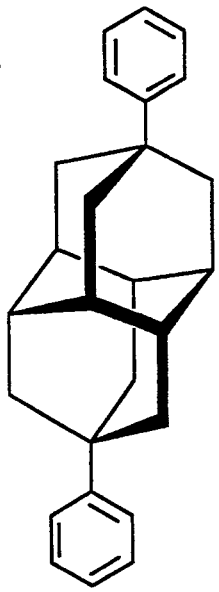
FIG. 11 is a simplified structural diagram of 4,9-diphenyldiamantane as synthesized in Example 12.
Figure 12:
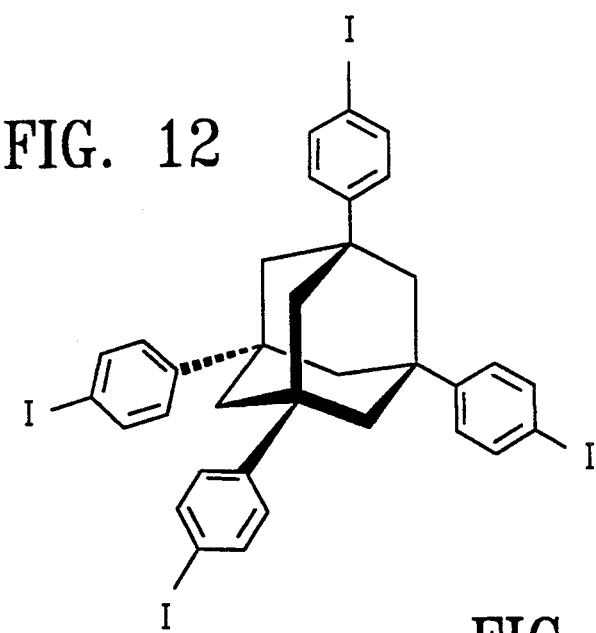
FIG. 12 is a simplified structural diagram of 1,3,5,7-tetra(p-iodophenyl)adamantane as synthesized in Example 13.
Figure 13:
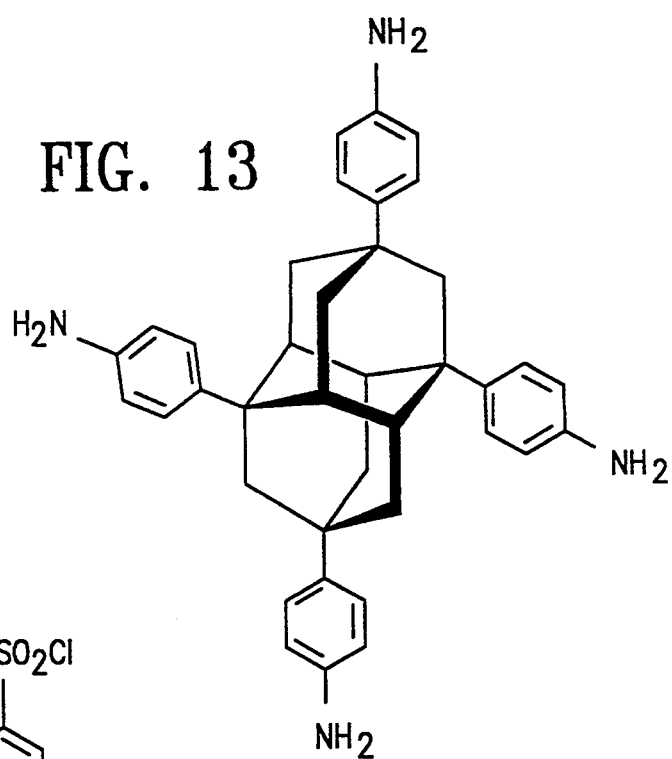
FIG. 13 is a simplified structural diagram of 1,3,5,7-tetra(p-aminophenyl)adamantane as synthesized in Example 14.
Figure 14:
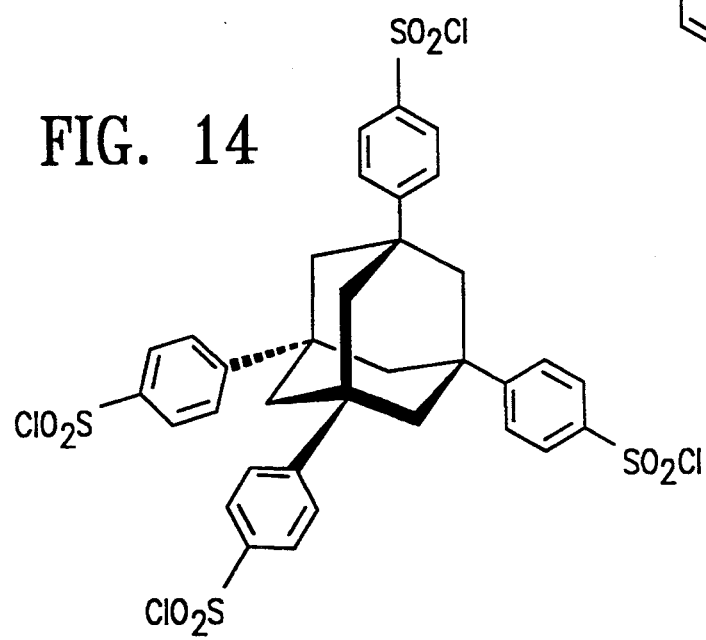
FIG. 14 is a simplified structural diagram of 1,3,5,7-tetra(phenyl-4-sulfonyl chloride)adamantane as synthesized in Example 15.
Figure 15:
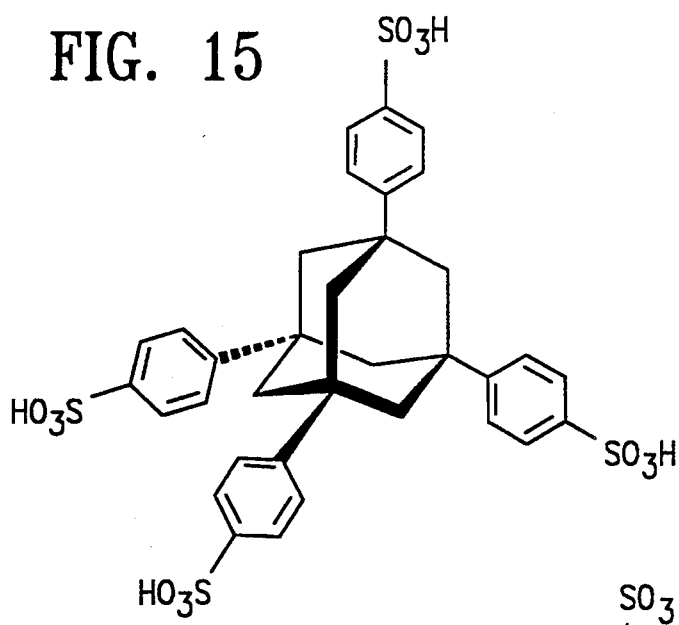
FIG. 15 is a simplified structural diagram of 1,3,5,7-tetra(phenyl-4-sulfonic acid)adamantane as synthesized in Example 16.
Figure 16:
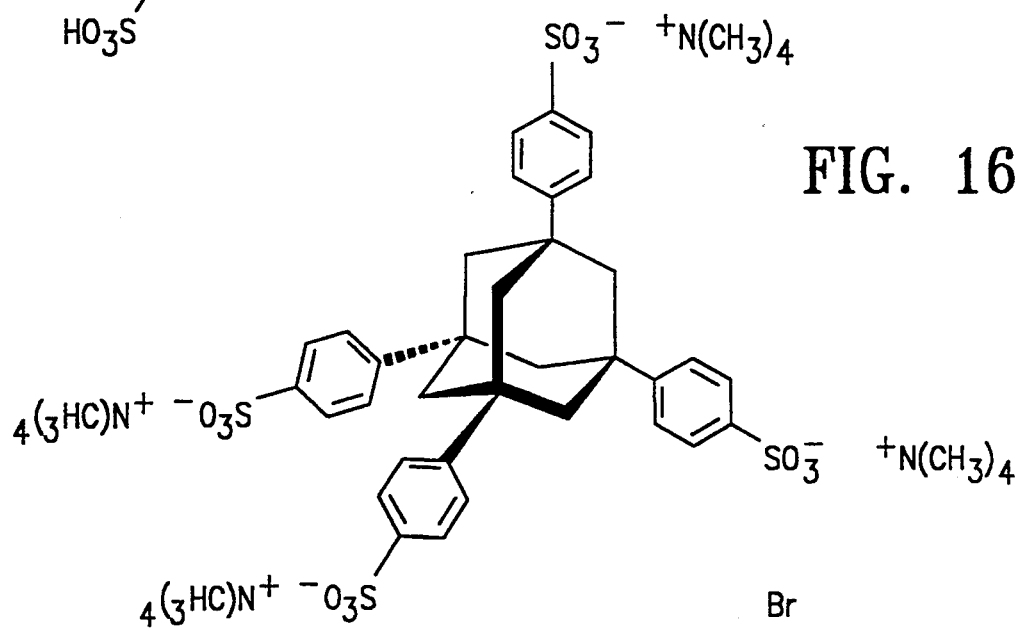
FIG. 16 is a simplified structural diagram of 1,3,5,7-tetra(phenyl-4-sulfonic acid-tetramethylammonium salt)adamantane as synthesized in Example 17.
Figure 18:
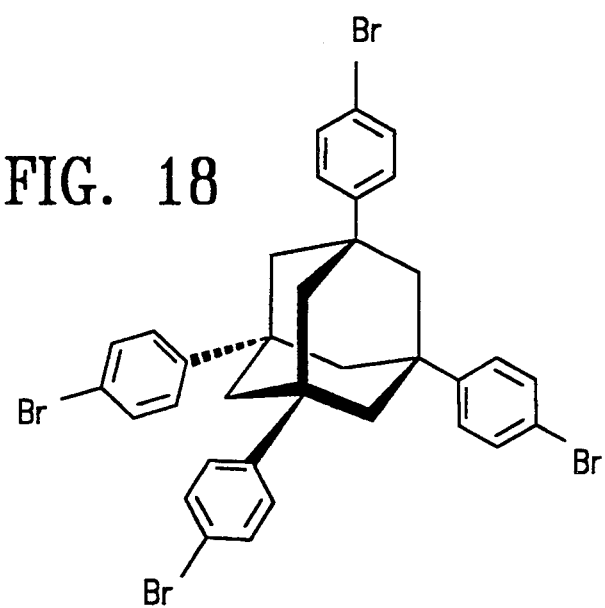
FIG. 18 is a simplified structural diagram of 1,3,5,7-tetra(4-bromophenyl)adamantane as synthesized in Example 19.
Figure 17:
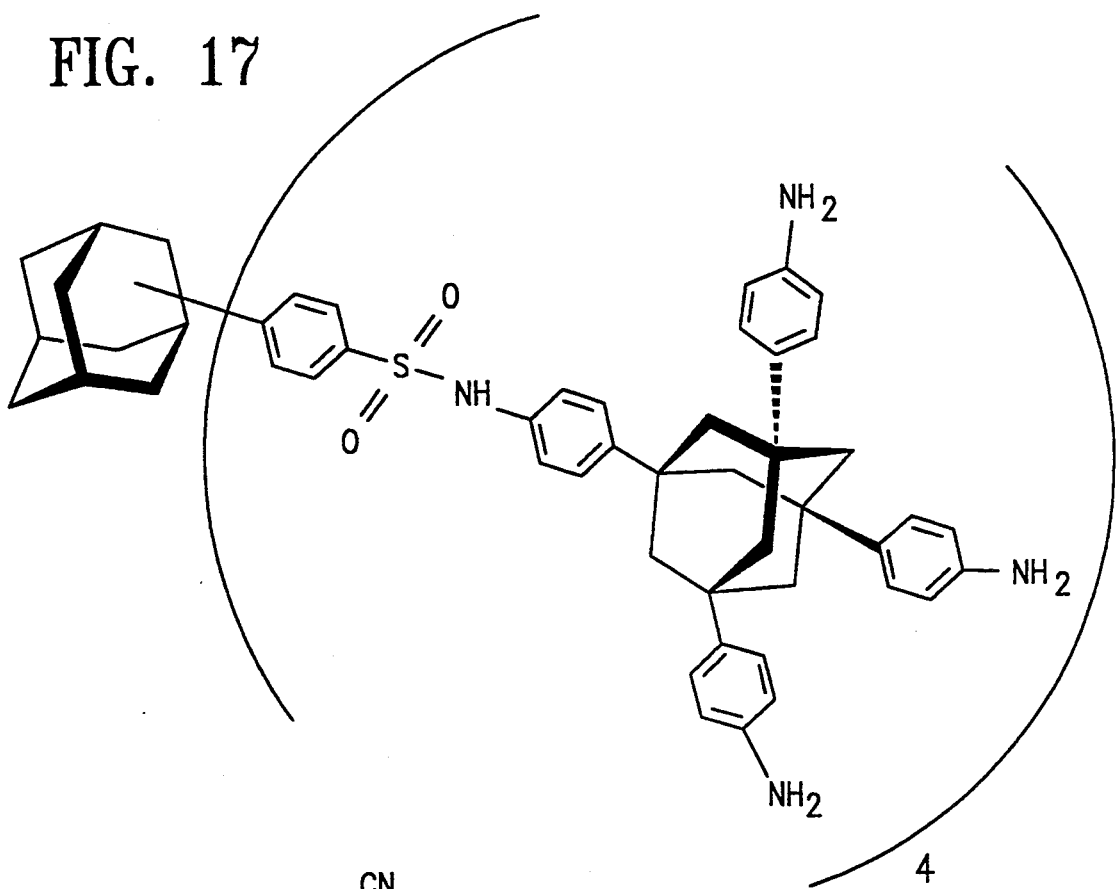
FIG. 17 is a stage-one dendrimer formed by reacting 1,3,5,7-tetra(p-aminophenyl)adamantane with 1,3,5,7-tetra(phenyl-4-sulfonyl chloride)adamantane according to the procedure of Example 18.
Figure 19:
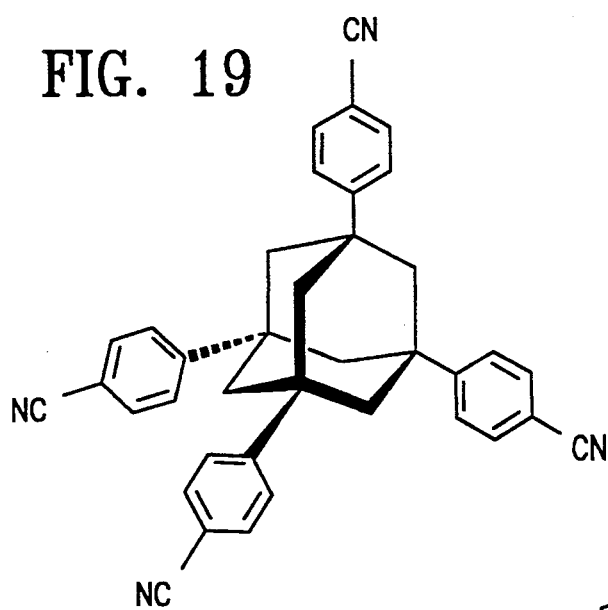
FIG. 19 is a simplified structural diagram of 1,3,5,7-tetra(4-cyanophenyl)adamantane as synthesized in Example 20.
Figure 20:
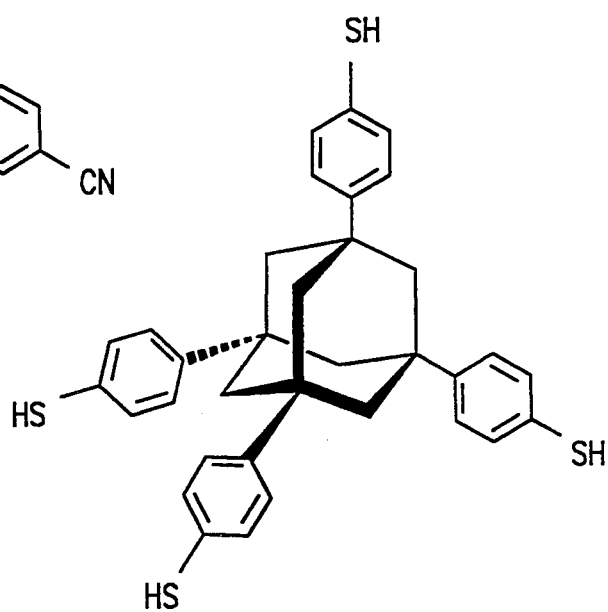
FIG. 20 is a simplified structural diagram of 1,3,5,7-tetra(4-mercaptophenyl)adamantane as synthesized in Example 22.
Figure 21:
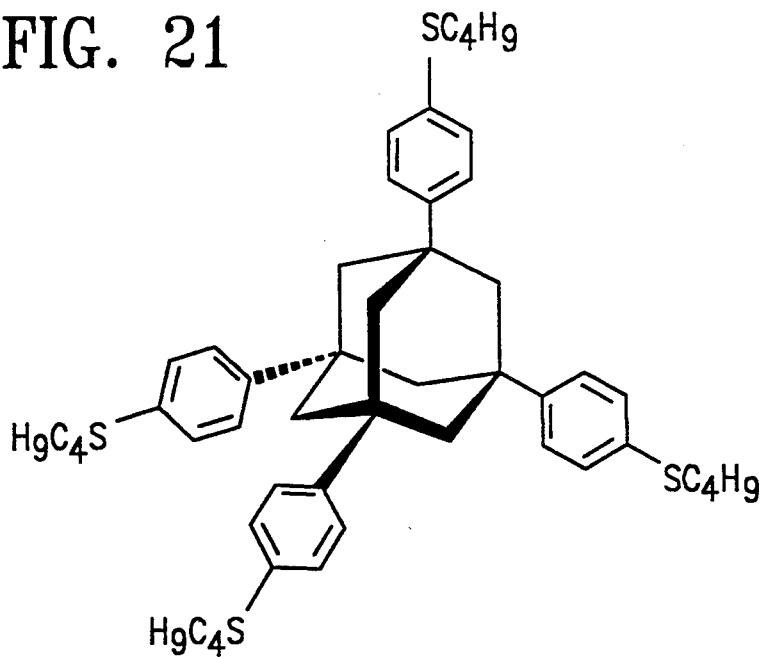
FIG. 21 is a simplified structural diagram of 1,3,5,7-tetra(n-butyl) sulfide tetraphenyl adamantane as synthesized in Example 23.
Figure 22:
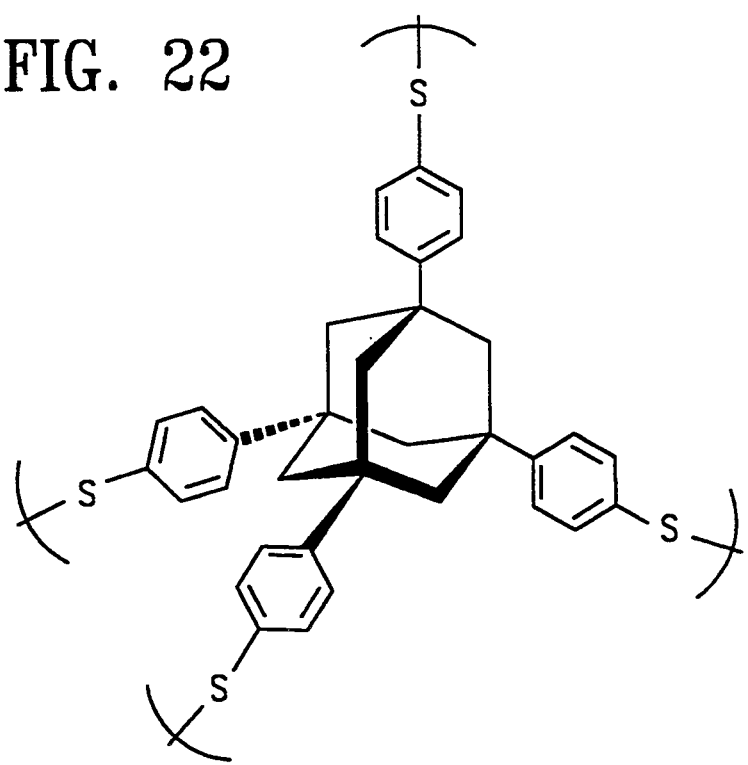
FIG. 22 is a simplified structural diagram of a polymer derived from the reaction of 1,3,5,7-tetra (4-mercaptophenyl)adamantane as described in Example 24.

Following the procedure of Example 1, the reaction of 32.0 grams of diamondoid mixture with 82.22 grams of t-butyl bromide in 250 mL of toluene with 1.645 grams of $AlCl_3$ gave 62.7 grams of oil after purification, with an average degree of arylation of 2.2 based on GC analysis. The gas chromatograms of the diamondoid feed mixture and the product oil are shown in FIGS. 2 and 3, respectively.

EXAMPLE 3

Following the procedure of Example 1, the reaction of 65.3 grams of diamondoid mixture with 107.0 grams of t-butyl bromide in 250 mL of o-xylene with 3.17 grams of $AlCl_3$ gave 94.0 grams of oil after purification, with an average degree of arylation of 1.7 based on GC analysis.

EXAMPLE 4

Following the procedure of Example 1, the reaction of 64.3 grams of diamondoid mixture with 137.7 grams of t-butyl bromide in 322 mL of xylenes with 3.38 grams of AlCl$_3$ gave 113.2 grams of oil after purification, with an average degree of arylation of 1.8 based on GC analysis.

EXAMPLE 5

Following the procedure of Example 1, the reaction of 52.0 grams of diamondoid mixture with 136.7 grams of t-butyl bromide in 250 mL of ethylbenzene with 2.82 grams of AlCl$_3$ gave 41.6 grams of oil after purification, with an average degree of arylation of 1.2 based on GC analysis.

EXAMPLE 6

Synthesis of 1,4,6,9-Tetraphenyldiamantane

To diamantane (10.8 g, 57.4 mmol) was added dry benzene (175 mL), t-butyl bromide (31.5 mL, 193 mmol), aluminum chloride (1.25 g). A condenser, with a calcium chloride drying agent was attached to the flask. The flask was placed in an oil bath at 120° C. After refluxing for 2.5 hr., the reaction was quenched with 200 mL of ice water. After adding diethylether (200 mL), the precipitate that formed was filtered and washed with additional diethylether (200 mL). The solid was placed in a thimble and purified with benzene in a soxhlet extractor. After seven days, 1,4,6,9-Tetraphenyldiamantane (19.4 g, 69%) was recovered from the thimble. $^1$H NMR (CDC1$_3$, 360 MHz) δ1.79 (s, 4H), 1.85, 1.89 (AB, 4H), 2.18 2.22 (AB, 4H), 2.87 (s. 4H), 7.05–7.48 (m, 20H) .

EXAMPLE 7

Synthesis of 1,4,6,9-Tetra(4-nitrophenyl)diamantane

A 50-mL round-bottom flask was charged with 13 mL of fuming nitric acid (90%). The flask was placed in a cold bath at −42° C. After 15 minutes, 1,4,6,9-Tetraphenyldiamantane (0.4 g, 0.81 mmol) was added. After stirring for 1.5 hr. the reaction was quenched by adding it to 50 mL of ice water. The solid was filtered and dried to yield 1,4,6,9-Tetra(4-nitrophenyl)diamantane (0.46 g, 83%). $^1$H NMR (CD$_2$Cl$_2$, 200 MHz) δ1.85 (s, 4H), 2.0–2.2 (two AB patterns), 2.99 (s, 4H), 7.35, 7.70, 8.02, 8.07, 8.23, 8.27 (two AA'BB' patterns, 16H).

EXAMPLE 8

Synthesis of 1,4,6,9-Tetra(4-aminophenyl)diamantane

To 1,4,6,9-tetra(4-nitrophenyl)diamantane (4.3 g, 6.4 mmol) was added tin chloride (SnCl$_2$—2H$_2$O, 26 g), ethanol (500 mL) and concentrated hydrochloric acid (100 mL). The mixture was refluxed and stirred for four days. The solution was cooled and made alkaline with sodium hydroxide. The solid was filtered and washed with boiling water (2 liters). The pale-yellow solid was dried to give 1,4,6,9-Tetra(4-aminophenyl)diamantane (3.5 g, 99%). $^1$H NMR (DMSO-d$_6$, 200 MHz) δ1.50 (s, 4H), 1.68, 1.91 (two AB patterns, 8H), 2.63 (s, 4H), 4.74 (s, 4H), 4.82 (s, 4H), 6.38, 6.42, 6.53, 6.57, 6.77, 6.81, 7.08, 7.12 (two AA'BB' patterns, 16H).

EXAMPLE 9

Synthesis of 1,4,6,9-Tetra(4-phenyl trimethylammonium iodide)diamantane

To 1,4,6,9-tetra(4-aminophenyl)diamantane (2.2 g, 4.0 mmol) was added methanol (350 mL), sodium bicarbonate (5.03 g, 70 mmol) and methyl iodide (6 mL). The mixture was stirred under reflux for 24 hours at which point an additional 5 ml of methyl iodide was added. After 48 hr. the solid formed during the reaction was filtered to give 1,4,6,9-Tetra(4-phenyl trimethylammonium iodide)diamantane (2.34 g, 48%). $^1$H NMR (DMSO-d$_6$, 200 MHz) δ1.69 (s, 4H), 1.7–2.2 (two AB patterns, 8H), 3.04 (s, 4H), 3.52 (s, 18H), 3.59 (s, 18H), 7.43, 7.47, 7.77, 7.91 (AA'BB", 16H).

EXAMPLE 10

Synthesis of 4,9-Di(4-bromophenyl)diamantane

To 4,9-diphenyldiamantane (5.0 g, 14.7 mmol) was added carbon tetrachloride (270 mL), freshly washed iron (1.64 g), bromine (1.51 mL, 29.4 mmol), and the mixture was stirred for 27 hours at room temperature. The mixture was transferred to a beaker containing water (200 mL) and stirred for 10 minutes. The solution was transferred to a separatory funnel, and the aqueous layer was discarded. The organic layer was washed with saturated sodium bicarbonate solution and distilled water. The organic layer was evaporated giving 4,9-di(4-bromophenyl)diamantane (6.1 g, 54%). The crude product was recrystallized from chlorobenzene. $^1$H NMR (CD$_2$Cl$_2$, 360 MHz) δ1.92, 1.96 (allphatic, 18H), 7.28, 7.30, 7.42, 7.45 (AA'BB', 8H).

EXAMPLE 11

Synthesis of 4,9-Di(4-iodophenyl)diamantane

To 4,9-diphenyldiamantane (13.5 g, 39.7 mmol) was added iodine (10.1 g, 39.7 mmol), bis-trifluoroacetoxy)iodobenzene (35.9 g, 83.4 mmol) and chloroform (270 mL). The mixture was stirred for 25 minutes at room temperature and then transferred to a beaker containing distilled water (400 mL) and stirred. Sodium hydrosulfite was added until the purple color disappeared. The solution was transferred to a separatory funnel, and the aqueous layer was discarded. The organic layer was washed with distilled water and evaporated to give 4,9-di(4-iodophenyl)diamantane (18.4 g, 78%). The product was recrystallized from chlorobenzene. $^1$H NMR (CDCl$_3$, 360 MHz) δ1.91, 1.95 (aliphatic, 18H), 7.13, 7.16, 7.62, 7.65 (AA'BB' 8H).

EXAMPLE 12

Synthesis of 4,9-Diphenyldiamantane

To diamantane (4.3 g, 22.8 mmol) was added benzene (51 mL), t-butylbromide (6.5 mL, 56.4 mmol), aluminum chloride (0.258 g 1.9 mmol) and the mixture was stirred at ambient temperature for 1 hour. The solid formed was filtered and washed with 200 mL of diethylether. The solid was dried and was identified by $^1$H NMR and $^{13}$C NMR as 4,9-diphenyldiamantane (6.5 g, 84%). The filtrate was washed with distilled water, and the ether was evaporated to give 1.8 g of a white solid. The solid was analyzed with CG-MS and consisted of 59% 4,9-diphenyldiamantane and 30% of triphenyldiamantane. $^1$H NMR (CD$_2$Cl$_2$ 360 MHz): of 4,9-diphenyldiamantane δ1.97 (s, 18H), aromatic/aliphatic ratio 5.9. 13C NMR (CD$_2$Cl$_2$, 360 MHz) 34.62 (-C-apical), 37.99, 43.87 (CH$_2$, CH), 125.50, 125.91, 128.48, 151.12 (phenyl).

EXAMPLE 13

1,3,5,7-Tetra(p-Iodophenyl)adamantane

A 100-mL round-bottom flask was charged with 1,3,5,7-tetraphenyladamantane (1.00 g, 2.3 mmol), iodine (2.33 g, 9.2 mmol), bis-trifluoroacetoxy) iodobenzene (4.5 g, 10 mmol) and chloroform (20 mL). The mixture was stirred at room temperature for 25 minutes and then transferred to a separatory funnel and washed four times with distilled water. The organic layer was evaporated, and the remaining solid was washed with diethylether to get rid of the purple color. The solid was recrystallized from chloroform and carbon tetrachloride (3:1) to give 1,3,5,7-tetra(p-iodophenyl)adamantane (1.5 g, 1.6 mmol, 69%). $^1$H NMR (CDCl$_3$, 360 MHz): d 2.05 (12H), 7.17, 7.19, 7.65, 7.67 (AA'BB', 16H). $^{13}$C NMR 148.40, 137.52, 127.11, 91.726 (aromatic), 46.67, 39.04 (aliphatic), FABMS m/z (M+944).

EXAMPLE 14

Synthesis of 1,3,5,7,-Tetra(4-aminophenyl)adamantane

To 1,3,5,7-tetra(p-nitrophenyl)adamantane (0.62 g, 1 mmol) was added 75 mL of ethyl alcohol followed by 15 mL of concentrated hydrochloric acid. Stannous chloride (SnCl$_2$—2H$_2$O, 4.1 g, 15 mmol), was added to the mixture. After refluxing for 48 hours, the solvent was evaporated and 15 mL of water was added. The aqueous solution was made basic by adding 3M NaOH and was extracted four times with 50 mL of THF. The solvent was evaporated and crude 1,3,5,7-tetra(4-aminophenyl)adamantane was collected (0.5 g, mmol, >90%). $^1$H NMR (DMSO-d$_6$, 360 MHz): of 1,3,5,7-tetra(4-aminophenyl)adamantane δ1.82 (s 12H), 4.79 (s 8H), 6.50, 6.52, 7.11, 7.13 (AA'BB', 16H). $^{13}$C NMR 37.77 (CH$_2$), 47.64 (C—Ph—NH$_2$), 113.65, 125.18, 137.60, 146.12 (Ph—NH$_2$).

EXAMPLE 15

Synthesis of 1,3,5,7-Tetra(phenyl-4-sulfonyl chloride)adamantane

A 100-mL round-bottom flask was charged with 20 mL of chlorosulfonic acid and cooled to 0° C. After 15 min., solid 1,3,5,7-tetraphenyladamantane (1.86 g, 4.2 mmol) was added slowly. The flask was stoppered, and the mixture was stirred. After 1.6 hr, the mixture was dumped onto 30 g of ice. The white solid was filtered and dried to give 1,3,5,7-tetra(phenyl-4-sulfonyl chloride)adamantane (2.8 g, 3.4 mmol, 80%). $^1$H NMR (CD$_3$CN, 200 MHz): of 1,3,5,7-tetra(phenyl-4-sulfonyl chloride)adamantane δ2.289 (s 12H), 7.894, 7.938, 8.075, 8.118 (AA'BB' 16H). $^{13}$C NMR 41.213 (CH$_2$), 45.822 (C—PhSO$_2$Cl), 128.188, 128.414, 142.889, 158.391 (PhSO$_2$Cl).

EXAMPLE 16

Synthesis of 1,3,5,7-Tetra(phenyl-4-sulfonic acid)adamantane

To 1,3,5,7-Tetra(phenyl-4-sulfonyl chloride)adamantane (0.55 g, 0.66 mmol), was added 15 mL of water, and the mixture was allowed to stir at room temperature for 5 days. The water was evaporated using high vacuum. A glassy solid, 1,3,5,7-Tetra(phenyl-s-sulfonic acid)adamantane (0.36 g, 0.47 mmol, 71%) remained.

EXAMPLE 17

Synthesis of 1,3,5,7-Tetra(phenyl-4-sulfonic acid-tetramethylammonium salt)adamantane To 1,3,5,7-Tetra(phenyl-4-sulfonic acid)adamantane (0.36 g, 0.47 mmol) dissolved in 10 mL of water was added tetramethylammonium hydroxide (0.4 g, 2.2 mmol). The water was evaporated and the glassy solid 1,3,5,7-Tetra(phenyl-4-sulfonic acid-tetramethylammonium salt)adamantane was isolted (0.52 g, 0.35 mmol, 74%). $^1$H NMR (CD$_3$OD, 200 MHz): of 1,3,5,7-Tetra(phenyl-4-sulfonic acid-tetramethylammonium salt)adamantane δ2.208 (s 12H), 3.148 (s 48H), 7.630, 7.668, 7.807, 7.846 (AA'BB', 16H).

EXAMPLE 18

Synthesis of Stage-One Dendrimer

To 1,3,5,7-Tetra-(4-aminophenyl)adamantane (0.48 g, 0.96 mmol) was added 40 mL of pyridine. To this mixture was added solid 1,3,5,7-Tetra(phenyl-4-sulfonyl chloride)adamantane (0.1 g, 0.12 mmol) and the mixture was stirred. After 48 hours at ambient temperature, the red precipitate was filtered and washed with tetrahydrofuran to give the stage-one dendrimer (0.19 g, 0.07 mmol, 58%). $^1$H NMR (DMSO-d$_6$, 360 MHz): of the stage-one dendrimer δ1.87 (s), 2.06 (s), 6.64, 6.67, 7.21, 7.24 (AA'BB'), 7.52, 7.53 (appears like quartet).

EXAMPLE 19

Synthesis of 1,3,5,7-Tetra(4-bromophenyl)adamantane

Iron powder (260.2 mg) was added to a suspension of 1.68 g of tetraphenyladamantane and 2.95 g of Br$_2$ in 150 mL of CS$_2$. After stirring for 48 hours, the red solution became clear. After filtering the reaction mixture and removing the solvent, the product crystallized from CHCl$_3$. $^1$H-NMR (CDCl$_3$, 200 MHZ)δ: AA'BB' 7.49, 7.45, 7.34, 7.30 (16H), 2.08 (12H). $^{13}$C-NMR: 146 ppm, 130 ppm, 125 ppm, 118.7 ppm 45.3 ppm, 37.5 ppm. Yield from crystallization: 45.1%. m.p. 354 ° C.

EXAMPLE 20

Synthesis of 1,3,5,7-Tetra (4-cyanophenyl)adamantane

A mixture of cuprous cyanide (190 mg) and tetra(4-bromophenyl)adamantane (302 mg) in 1 mL of DMF was heated with stirring under reflux for 3.5 hours. A mixture of ethanol (2 mL) and ferric chloride (60% solution, 2 mL) was added to quench the reaction after it had cooled to room temperature. The resulting mixture was heated to the boiling point briefly, cooled, and then added to a stirred HCl solution (20 mL of concentrated HCl and 80 mL of distilled water). Extraction of the solution with 20 mL of methylene chloride twice, evaporation of the solvent, and column chromatography using methylene chloride as the solvent gave a white solid, tetra(4-cyanophenyl)adamantane. $^1$H NMR(CD$_2$Cl$_2$, 200 MHZ): 7.71, 7.67, 7.61, 7.57 (AA'BB' 16H) 2.17 (12H). $^{13}$C-NMR: 153.7, 132.8, 126.3, 119.0, 110.9, 46.4, 40.1 ppm.

EXAMPLE 21

Synthesis of Cu$^I$[1,3,5,7-tetra-4-cyanophenyl)adamantane]BF$_4$XC$_6$H$_5$NO$_2$ A solution of Cu(CH$_3$CN)$_4$BF$_4$ (22 mg) and tetra(4-cyanophenyl)adamantane ca 0.5 C$_6$H$_6$ (40 mg) in CH$_3$CN (1.5 mL) was diluted with PhNO$_2$ (20 mL). The solution was allowed to evaporate at room temperature in an open beaker giving colorless transparent crystals after 3 days.

EXAMPLE 22

Synthesis of 1,3,5,7-Tetra(4-Mercaptophenyl)adamantane

To a 100 mL 3-neck flask containing 7.52 g NaH, was added 36 mL 1-Methyl-2-pyrrolidone (NMP) under nitrogen protection. After cooling in an ice water bath, 20 mL of n-BuSH was added slowly over two hours. When the reaction calmed down 4.23 g of tetra(4-bromophenyl)adamantane was added. After refluxing for two days, the reaction was quenched with ice cold HCl in water (50:50). Filtration gave a gray powder which on stirring with 50 mL MeOH, and a second filtration gave 1.17 g of product. Yield: 36.7% $^1$H NMR (CD$_2$Cl$_2$, 200 MHZ): 7.37, 7.33, 7.28, 7.24 (AA'BB' 16H), CH$_2$ of adamantane 2.05 (12H), SH 3.50 (4H).

EXAMPLE 23

Synthesis of 1,3,5,7-Tetra(n-Butyl)sulfide tetraphenyladamantane n-BuSNa (5 mL) is transferred to a 25 mL flask containing 1,3,5,7-tetra(4-bromophenyl)adamantane (755.6 mg, 1 mmol). The mixture is refluxed under nitrogen for 20 hours. Later the reaction mixture is cooled to room temperature. A 50% solution of hydrogen chloride (1.5 mL) was added to the mixture until the pH was 2, then another 2–3 mL of water was added. The solution was extracted with 3 mL of ethyl ether, three times. The solvent was evaporated from the ether extract. A TLC was performed using 40% CH$_2$Cl$_2$ and 60% hexane as the developing reagent. NMR analysis showed that the major product in the first fraction was 1,3,5,7-tetra(4-n-butylmercaptophenyl adamantane. $^1$H NMR: (CD$_2$Cl$_2$, 200 MHZ) 7.43, 7.38, 7.32, 7.27 (AA'BB' 16H), 2.00 (12H), 2.91 (t.8H) 1.26≈1.56 (m.16H) 0.91 (t.12H).

EXAMPLE 24

Synthesis of the 1,3,5,7-Tetra(4-mercaptophenyl)adamantane Polymer

Tetra(4-mercaptophenyl)adamantane (150 mg) was dissolved in THF (12 mL). 2 mL of 10% KHCO$_3$ was added. Gradually bromine (≈120 mg) was added, and a gray precipitate, the polymer, formed immediately; the color of the powdery product depends on how much bromine is added. $^{13}$C NMR (Solid State): 148.8, 125.72, 134.5 (shoulder) 38.80. TGA:
(90% wt) 439.3° C.
N$_2$.40 ml/min.
IR:
558.2 cm$^{-1}$ (s-s stretch)
625.7 cm$^{-1}$ (c-s stretch)
827.5 cm$^{-1}$ (p-substituted aromatic ring)

Changes and modifications in the specifically described embodiments can be carried out without departing from the scope of the invention which is intended to be limited only by the scope of the appended claims.

What is claimed is:

1. A method for arylating a diamondoid compound comprising the steps of:
   (a) providing a non-halogenated diamondoid compound or mixture of non-halogenated diamondoid compounds and an aromatic compound or mixture of aromatic compounds wherein at least one diamondoid compound and at least one aromatic compound are at least partially miscible;
   (b) mixing the compounds of step (a) to form at least a partial solution;
   (c) providing a reactive halide source selected from the group consisting of alkyl halides, benzyl halides, and allylic halides in the mixture of step (b);
   (d) adding a Lewis acid to said mixture of step (c);
   (e) heating said mixture of step (d) to temperature above ambient and holding said heated mixture at elevated temperature;
   (f) recovering an arylated diamondoid compound from said solution.

2. The method of claim 1 further comprising heating said solution of step (d) to at least about 50° C.

3. The method of claim 1 further comprising providing at least one mole of said aromatic solvent per mole of diamondoid compound.

4. The method of claim 1 further comprising providing at least one mole of said aromatic solvent per mole of aryl substitutent in the desired arylated diamondoid product.

5. The method of claim 1 further comprising providing at least four moles of said aromatic solvent per mole of said diamondoid compound of step (a).

6. The method of claim 1 further comprising arylating said diamondoid compound in the absence of an intermediate product recovery step.

7. The method of claim 1 further comprising arylating said diamondoid compound in the absence of a step to recover a halide or alcohol of said diamondoid compound of step (a).

8. The method of claim 1 wherein said reactive halide source comprises an alkyl halide.

9. The method of claim 8 wherein said alkyl halide comprises a tertiary alkyl halide.

10. The method of claim 1 wherein said Lewis acid is selected from the group consisting of AlCl$_3$, FeCl$_3$, SnCl$_4$, ZnCl$_2$, TiCl$_4$, FeBr$_3$, SnBr$_4$, ZnBr$_2$, and TiBr$_4$.

11. The method of claim 10 wherein said Lewis acid is AlCl$_3$.

12. The method of claim 2 further comprising heating said mixture of step (d) to temperature of from about 75° to about 125° C.

13. The method of claim 1 further comprising no intermediate product recovery step.

14. A method for arylating a diamondoid compound comprising the steps of:
   (a) providing a non-halogenated diamondoid compound or mixture of non-halogenated diamondoid compounds and an aromatic compound or mixture of aromatic compounds wherein at least one diamondoid compound and at least one aromatic compound are at least partially miscible;
   (b) mixing the compounds of step (a) to form at least a partial solution;
   (c) adding t-butyl halide to said mixture of step (b);
   (d) adding AlCl$_3$ or AlBr$_3$ to said mixture of step (c);
   (e) heating said mixture of step (d) to temperature above ambient and holding said heated mixture at elevated temperature;
   (f) recovering an arylated diamondoid compound from said solution in the absence of an intermediate product recovery step.

15. A method for selectively producing phenyl-substituted diamantane comprising the steps of:
   (a) mixing non-halogenated diamantane with an aromatic compound or mixture of aromatic compounds comprising at least one member which is at least partially miscible with said non-halogenated diamantane;
   (b) adding t-butyl halide to said mixture of step (a);
   (c) adding AlCl$_3$ or AlBr$_3$ to said mixture of step (b);
   (d) heating said mixture of step (d) to temperature above ambient and holding said heated mixture at elevated temperature; and
   (e) recovering phenyl-substituted diamantane from said solution in the absence of an intermediate product recovery step.

16. The method of claim 15 wherein the molar ratio of t-butyl halide to non-halogenated diamantane is from about 1.5:1 to about 4:1 and wherein step (e) further comprises recovering 4,9-diphenyl-diamantane in the absence of an intermediate product recovery step.

17. The method of claim 15 wherein the molar ratio of t-butyl halide to non-halogenated diamantane is from about 2:1 to about 5:1 and wherein step (e) further comprises recovering 1,4,6,9-tetraphenyl-diamantane in the absence of an intermediate product recovery step.

* * * * *